United States Patent [19]
Willay et al.

[11] 4,401,625
[45] Aug. 30, 1983

[54] APPARATUS FOR PREPARING TEST SAMPLES

[75] Inventors: Gerard Willay, Ars sur Moselle; Andre Wittmann, Metz, both of France

[73] Assignee: Institut de Recherches de la Siderurgie Francaise, Saint-Germain-en-Laye, France

[21] Appl. No.: 284,453

[22] Filed: Jul. 17, 1981

[30] Foreign Application Priority Data

Jul. 24, 1980 [FR] France .................. 80 16410

[51] Int. Cl.³ .............................. G01N 1/28
[52] U.S. Cl. ................... 422/50; 422/68; 422/102; 422/240; 432/264; 436/174
[58] Field of Search ............ 156/83; 432/264; 422/68, 102, 50, 248, 199, 240, 241

[56] References Cited

U.S. PATENT DOCUMENTS 2,665,223 1/1954 Clough et al. .................. 432/264
4,159,891 7/1979 Schmidt et al. ............. 156/DIG. 83
4,272,488 6/1981 Carman ......................... 422/199

FOREIGN PATENT DOCUMENTS 2381303 9/1981 France .

Primary Examiner—Michael S. Marcus
Attorney, Agent, or Firm—Michael J. Striker

[57] ABSTRACT

An apparatus for preparing test samples for chemical analytical testing has an electric coil adapted to receive a crucible and connected to a source of electricity. The crucible is formed by an outer vessel of a noble metal and by an inner vessel formed of a rigid refractory material that is a good conductor of heat and that is not wettable by the sample. Normally platinum or a platinum alloy is used for the outer vessel and vitreous carbon is used for the inner vessel. The apparatus further comprises a high-frequency electricity supply for supplying electricity to the coil and thereby heating the crucible and the sample therein, a casting receptacle at a lower station below the upper station and adapted to receive the melted sample, a dissolving receptacle at the lower station, and a bath of a solvent for the sample in the dissolving receptacle.

9 Claims, 1 Drawing Figure

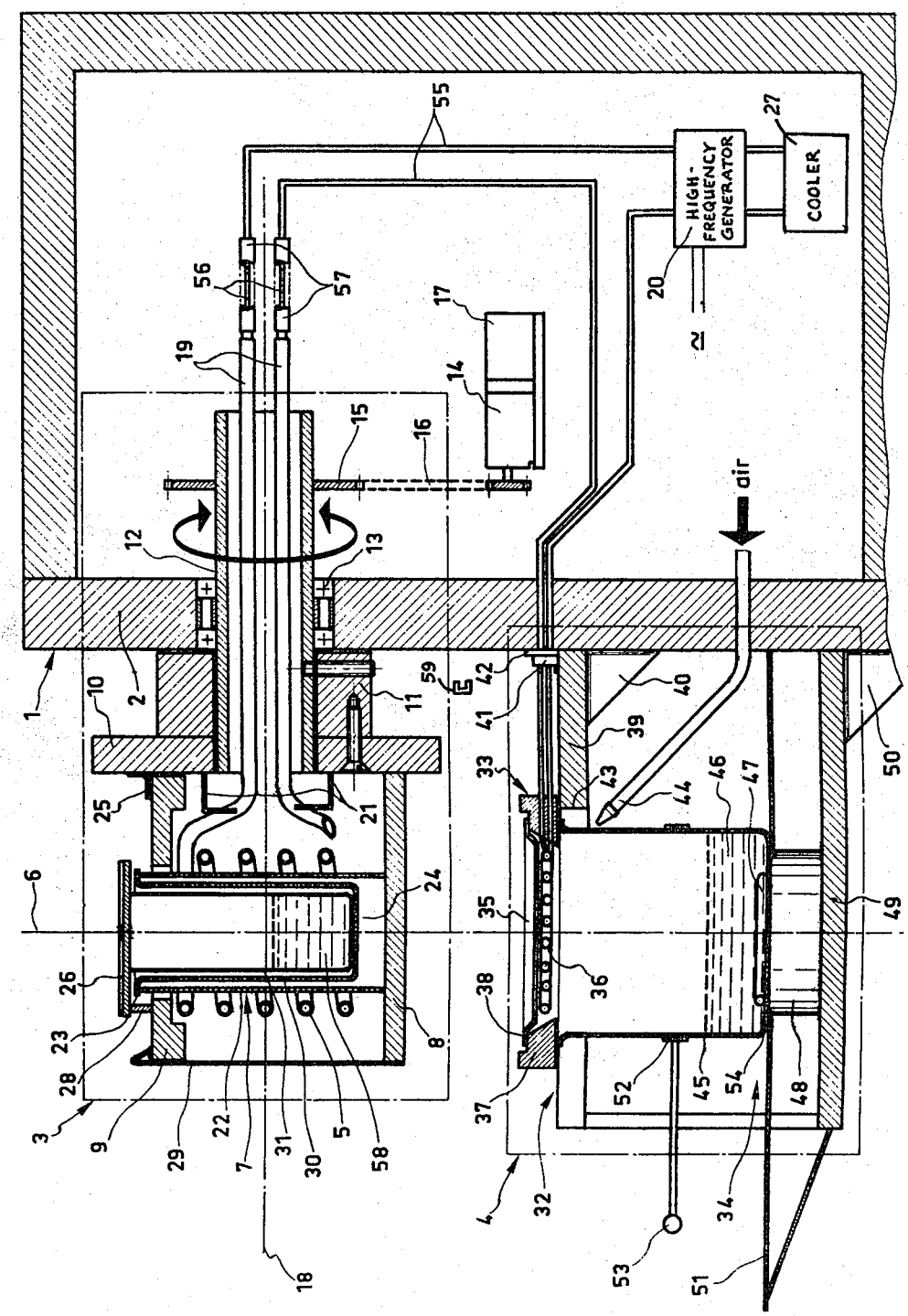

APPARATUS FOR PREPARING TEST SAMPLES

FIELD OF THE INVENTION

The present invention relates to an apparatus for preparing samples suitable for chemical analytical testing. More particularly this invention concerns such an apparatus used for melting and subsequently either casting or dissolving the melted sample.

BACKGROUND OF THE INVENTION

French Pat. No. 2,381,303 filed Feb. 12, 1977 describes an apparatus which basically comprises an upper sample-melting unit and a lower sample-preparing unit. The upper unit has an induction coil that is energized with high-frequency electricity and that surrounds a crucible in which the sample to be melted is held, normally mixed with a highly oxidizing material that serves to dilute and melt the sample. The lower unit primarily consists of a mold into which the fused material is poured from the upper unit to produce a casting that can then be tested. The melting crucible must be made of a noble metal such as platinum or a platinum alloy which is highly conductive and which will not react with the sample.

Since the noble metals used for the crucible are somewhat wettable by their contents, some of the sample is lost to the crucible. Thus when the fused sample is poured out, it does not have the same volume it originally had. As a result this type of sample preparation can only be used with test methods which do not need complete recovery of the sample after its fusion, as for example x-ray analyses. Such analysis methods as optical spetrometry cannot be used. Furthermore the extremely expensive platinum or platinum-gold alloy crucible has a relatively short service life, so sample preparation with it is quite expensive.

OBJECTS OF THE INVENTION

It is therefore an object of the present invention to provide an improved crucible for such a sample-preparation apparatus.

Another object is the provision of an improved sample-preparation apparatus which overcomes the above-given disadvantages.

SUMMARY OF THE INVENTION

These objects are attained according to the instant invention in an apparatus for preparing a test sample that has an electric coil adapted to receive a crucible and connected to a source of electricity, and that uses a crucible formed by an outer vessel of a noble metal and by an inner vessel formed of a rigid refractory material that is a good conductor of heat and that is not wettable by the sample. The term "noble" applied to a metal means that the metal is one that does not oxidize or that oxidizes very little when heated and exposed to air. Normally platinum or a platinum alloy is used for the outer vessel and vitreous carbon is used for the inner vessel.

The apparatus according to the invention further comprises means for supplying electricity to the coil and thereby heating the crucible and the sample therein, a casting receptacle at a lower station below the upper station and adapted to receive the melted sample, a dissolving receptacle at the lower station, and a bath of a solvent for the sample in the dissolving receptacle. Thus the melted sample can either be cast in the casting recepticle or dumped into and dissolved in the dissolving receptacle.

Although it is possible simply to provide a refractory lining in a noble-metal crucible, it has been found most economical when, according to this invention, the inner vessel is nested in the outer vessel so that it receives heat from the outer vessel purely by conduction and radiation. The inner vessel is normally somewhat taller than the outer vessel to facilitate pouring out the contents without getting any on the outer vessel. Since the refractory inner vessel is not wettable by the sample, 100% of the sample will be recovered, making the system of the instant invention usable with plasma-excited optical spectrometry.

According to further features of this invention the apparatus comprises a support for the dissolving receptacle, a magnetic mixing element in the dissolving receptacle, and a magnetic agitator in the support for the mixing element. Thus when the system is used to dissolve the melted sample, rather than to cast it, the sample can be thoroughly mixed with the solvent immediately as it is poured into it.

The casting receptacle in accordance with another feature of this invention is at least partially of a noble metal, lies above the dissolving receptacle, and is provided with a preheating coil connected to the means for supplying electricity. This preheating coil is generally planar and the dissolving receptacle is a flat dish sitting on the preheating coil. Furthermore the coils are connected in series so that the same high-frequency source of electricity can be connected to both of them, making a substantial saving in equipment costs. The coils are formed principally as copper tubes and are provided with means for circulating a fluid coolant through the tubes to avoid excessive heat buildup in these coils.

Although the refractory inner vessel is not strictly necessary when a sample is being prepared for plasma-excited spectrometry, it has been found advantageous to use it anyhow. It protects the expensive platinum-alloy outer vessel, as for instance when the sample contains zinc which could attack the platinum. Pouring a casting from a carbon vessel does indeed disperse iron and other oxidizable elements in the sample, because the reducing atmosphere due to the presence of carbon can somewhat inhibit oxidation of the sample by oxidizing compounds of the melt, such as lithium borate ($Li_2B_4O_7$) and the like. This problem is of course present when pouring into a beaker containing an acid solvent, but in this case the variation in the results is almost nothing thanks to the effect of the normalization in the acid solution.

Even though the inner vessel is not always completely indispensable, although normally advantageous and advisable, the same cannot be said for the outer noble-metal vessel. An apparatus set up and virtually tuned for a noble-metal vessel will not work with a nonmetallic vessel. The source of electricity would have to have a wholly different type of output, or a second source of electricity would have to be provided for use with a refractory vessel. Obviously such duplication of parts complicates the apparatus and raises its cost. In addition the relatively sturdy outer metal vessel physically protects the inner and substantially more fragile vessel. Furthermore the platinum outer vessel protects the inner carbon vessel from oxidation. This inner vessel could be held in a neutral atmosphere, but the costs of doing so would again be elevated.

A further obvious advantage of the system according to the instant invention is that it can be used at substantially less cost per test than the hitherto known systems. Normally when platinum-alloy crucibles are used in the standard arrangement—without a lining—they are returned to the supplier when they become so eroded that they are no longer usable. The supplier credits the laboratory with normally about 75% of the metallic value for the returned crucibles. The cost per test normally works out to about $2 for the crucible alone. When an inner vessel 1 mm thick of vitreous carbon is used, however, it is possible to reduce this cost by some 70%, mainly because the outer platinum vessels lasts much longer and the inner carbon vessels are quite cheap.

DESCRIPTION OF THE DRAWING

The above and other objects, features, and advantages will become more readily apparent from the following, reference being made to the accompanying drawing whose sole FIGURE is a partly schematic vertical section through the apparatus according to this invention.

SPECIFIC DESCRIPTION

The apparatus according to this invention has a housing 1 on whose front wall 2 is mounted an upper melting unit 3 and a lower preparation unit 4. The upper unit 3 has a generally cylindrical coil 5 centered on an upright axis 6 passing through both units and surrounding a crucible indicated generally at 7. A support 8 for the crucible 7 has a horizontal top plate 9 fixed by a hinge 25 to a vertical mounting plate 10 fixed on a block 11 mounted on a tubular arbor 12 centered on a horizontal axis 18 and rotatable thereabout with the crucible support 8 on a bearing 13 in the front wall 2. A reversible electric motor 14 is connected via a chain 16 to a sprocket 15 carried on the tubular arbor 12 and can be operated by an electronic controller 17 as will be described below to rock the crucible 7 through about 60° back and forth about the axis 18.

The cylindrical coil 5 is formed of hollow copper tubing having ends 19 held by supports 21 and extending out through the arbor 12 to a high-frequency electricity generator 20.

The crucible 7 is surrounded by a cylindrical refractory shield 22 of silica standing on the bottom plate 8 and having an upper edge on which a lip 23 of the crucible 7 stands. Thus an insulating dead-air space 24 is formed between the crucible 7 and the shield 22. A cover 26 for the crucible 7 stands on spacers 28 on the upper plate 9 and upwardly closes the crucible 7. A metallic elastic clip 29 fixed at its lower end on the fixed bottom plate 8 holds the hinged top plate 9 in the illustrated position.

The crucible 7 itself comprises a platinum-gold alloy outer vessel 30 of cylindrical shape and formed with the lip 23 and a vitreous-carbon inner vessel 31 that is also cylindrical and received with slight pray within the outer vessel 30. The inner vessel 31 is slightly taller than the outer vessel, so that the cover 26 rests on it. A collar may be provided around the inner vessel 31 to seal the space between it and the outer vessel 30 and thereby reduce oxidation of the outer surface of the inner vessel 31. Although the vessels 30 and 31 are both cylindrical, it is possible to make them of any other convenient shape, such as of square section.

The lower unit 4 has an upper casting assembly 32 and a lower dissolving assembly 34. The upper assembly 32 has an annular ceramic support block 37 formed with a shoulder 38 on which rests the lip of a casting receptacle or dish 35. A flat copper-tube coil 36 is fixed on this block 37 and has plugs 41 fitted into sockets 42 on the front wall 2 of the housing 1. The block 37, plate 35, and coil 36 form a removable casting assembly 33 that rests on an upper support plate 39 secured by means of a bracket 40 on the front wall 2. This support plate 39 is formed with a U-shaped cutout 43 underneath the block 37. An air hose 44 can direct a stream of compressed air at the bottom of the dish 35 to cool a molten-metal body therein.

The lower assembly 34 has a beaker 45 containing a body 46 of acid and provided with a ring 52 carrying a handle 53. This beaker 45 sits on a slide table 51 formed with a cutout 54 into which fits the upper end of a standard magnetic mixer 48 that coacts with a magnetic bar 47 inside the beaker 45 and that sits on a lower support plate 49 securd by a bracket 50 to the front wall 2.

The two coils 5 and 36 are connected in series by hollow copper lines 55 connected to the high-frequency generator 20 and to a cooler 27 that can circulate water through the tubes constituting these lines 55 and the coils 5 and 36. In order to allow the coil 5 to be rocked about the axis 18 by the motor 14, flexible copper conductors 56 and flexible elastomeric jackets 57 connect the lines 55 to the ends 19 of the coil 5 so that at this location the cooling water flows around the conductors 56.

The apparatus described above functions as follows:

A sample 58 is charged into the crucible 5 along with a quantity of a highly oxidizing dilutant such as lithium tetraborate. The source 20 energizes the coil 5 (and the coil 36) with electricity at several megahertz. This action heats the outside vessel 30 which heats the inner vessel 31 by radiation and conduction. At the same time the controller 17 operates the motor 14 to rock the entire upper assemby 3 back and forth through about 60°. After normally about one minute, approximately the same time as in a system without the inner vessel, the sample is fully melted.

In order to make a casting suitable for x-ray analysis, the motor 14 then pivots the upper assembly 3 through about 120° to pour the melt 58 into the dish 35 which has meanwhile been preheated by the coil 36. For such an operation the beaker 45 is not in position in the cutout 43. Once the melt is all in the dish 35 the high-frequency generator 20 shuts off, allowing the coil 36 to cool, and air is blown on the underside of the dish 35 from the nozzle 44. This cools the dish 35 and forms the melt therein into an ingot or casting suitable for testing. This casting can be dropped right out of the dish 35 simply be removing it from the block 37 and turning it over.

In order to make a liquid sample for spectroscopic analysis, the entire assembly 33 is withdrawn by unplugging from the sockets 42 and a U-shaped tubular copper jumper 59 is plugged into these sockets 42 to insure continuity of the electric and coolant lines. The beaker 45 is slid in on the table 51 through the U-shaped cutout 43 and the agitator 48 is energized to start the magnetic bar 47 spinning in the hydrochloric-acid bath 46. Thus when the upper assembly 3 is pivoted it will pour the melt 58 into the beaker 45. On contact with the liquid of the bath 46 the melt 58 will solidify, and then dissolve as it is mixed with the acid to produce a sample suitable for spectrophotographic analysis.

The system according to the instant invention therefore allows samples to be prepared for various types of analysis. If only one type of analysis is used, the upper or lower assembly 32 or 34 can be eliminated. Similarly it is possible to mount the unit 33 comprised of the block 37, dish 35, and coil 36 on an appropriate swivel or hinge connection to allow the opening 43 to be uncovered, rather than to make it wholly removable as illustrated.

We claim:

1. An apparatus for preparing a test sample comprising:
    a support defining an upper melting station and a lower station,
    an electric coil on said support at said upper melting station;
    a crucible receivable in said coil and formed by an outer vessel at least partially of a noble metal and by an inner vessel formed of a rigid refractory material that is a good conductor of heat and that is not wettable by said sample; means for supplying electricity to said coil and thereby heating said crucible and the sample therein for melting the sample;
    a dissolving receptacle at said lower station;
    a bath of a solvent for said sample in said dissolving receptacle;
    a magnetic mixing element in said dissolving receptacle;
    a magnetic agitator in said support for said mixing element; and
    means for tipping said crucible about a horizontal axis relative to said support and thereby pouring the melted sample in said crucible down into said receptacle in said lower station.

2. The apparatus defined in claim 1 wherein said refractory material is vitreous carbon.

3. The apparatus defined in claim 2 wherein said noble metal is platinum.

4. The apparatus defined in claim 3 wherein said inner vessel is snugly nested in said outer vessel.

5. The apparatus defined in claim 1, further comprising
    a casting receptacle at least partially of a noble metal,
    structure on said support supporting said casting receptacle in said lower station above said dissolving receptacle, said casting receptacle lying between said crucible and said dissolving receptacle when on said structure but being removable therefrom, whereby when on the structure said casting receptacle can receive the melted sample from the crucible but when not on the structure the melted sample is poured into the dissolving receptacle from the crucible, and
    means including a preheating coil on said casting receptacle and connected to said means for supplying electricity for preheating the casting receptacle.

6. The apparatus defined in claim 5 wherein said coils are connected in series.

7. The apparatus defined in claim 6 wherein said coils are formed principally as copper tubes and are provided with means for circulating a fluid coolant through said tubes.

8. The apparatus defined in claim 5 wherein said preheating coil is generally planar and said casting receptacle is a flat dish sitting on said preheating coil.

9. An apparatus for preparing a test sample comprising:
    a support defining an upper melting station and a lower station;
    an electric oil on said support at said upper melting station;
    a crucible receivable in said coil and formed by an outer vessel at least partially of a noble metal and by an inner vessel formed of a rigid refractory material that is a good conductor of heat and that is not wettable by said sample;
    means for supplying electricity to said coil and thereby heating said crucible and the sample therein for melting the sample;
    a dissolving receptacle at said lower station below said upper station, said receptacle being adapted to receive the melted sample;
    a bath of a solvent for said sample in said dissolving receptacle;
    a magnetic mixing element in said dissolving receptacle;
    a magnetic agitator in said support for said mixing element; and
    means for tipping said crucible about a horizontal axis relative to said support and thereby pouring the melted sample in said crucible down into said receptacle in said lower station.

* * * * *